(12) United States Patent
Guillard et al.

(10) Patent No.: US 7,229,639 B2
(45) Date of Patent: Jun. 12, 2007

(54) IBUPROFEN CONTAINING HARD SHELL CAPSULES

(75) Inventors: Emmanuelle Mireille Guillard, Colmar Cedex (FR); Nicolas Madit, Colmar Cedex (FR); Robert Anthony Scott, Bornem (BE)

(73) Assignee: Warner-Lambert Company, New York, NY (US)

( * ) Notice: Subject to any disclaimer, the term of this patent is extended or adjusted under 35 U.S.C. 154(b) by 498 days.

(21) Appl. No.: 10/384,230

(22) Filed: Mar. 7, 2003

(65) Prior Publication Data
US 2003/0211145 A1 Nov. 13, 2003

(30) Foreign Application Priority Data
Mar. 11, 2002 (EP) .................................. 02290595

(51) Int. Cl.
*A61K 9/48* (2006.01)
*A61K 9/64* (2006.01)
*A61K 9/66* (2006.01)

(52) U.S. Cl. ........................ 424/451; 424/455; 424/456

(58) Field of Classification Search .................. None
See application file for complete search history.

(56) References Cited

U.S. PATENT DOCUMENTS

| 5,360,615 | A | | 11/1994 | Yu et al. |
| 5,376,688 | A | | 12/1994 | Morton et al. |
| 5,912,011 | A | * | 6/1999 | Makino et al. ............. 424/455 |
| 6,008,192 | A | * | 12/1999 | Al-Razzak et al. ........... 514/11 |
| 6,211,391 | B1 | * | 4/2001 | Grubbs et al. ................ 556/21 |
| 6,221,391 | B1 | * | 4/2001 | Rouffer ....................... 424/456 |
| 2003/0105141 | A1 | * | 6/2003 | Gao et al. .................... 514/341 |

FOREIGN PATENT DOCUMENTS

WO  WO 9734585 A1 * 9/1997

* cited by examiner

*Primary Examiner*—Susan Tran
(74) *Attorney, Agent, or Firm*—Steve Zelson; Rosemary Miano

(57) ABSTRACT

The present invention relates to pharmaceutically acceptable and stable compositions, which are preferably clear transparent, for liquid filling hard shell capsules, hard shell capsules containing these compositions, and a process for preparing these hard shell capsules and whereby the shells of said hard capsules are preferably clear transparent.

9 Claims, No Drawings

IBUPROFEN CONTAINING HARD SHELL CAPSULES

This application claims priority to EP02290595.4 filed Mar. 11, 2002.

DESCRIPTION

The present invention relates to pharmaceutically acceptable and stable compositions, which are preferably clear transparent, for liquid filling hard shell capsules, hard shell capsules containing these compositions, and a process for preparing these hard shell capsules and whereby the shells of said hard capsules are preferably clear transparent.

Ibuprofen (2-(4-isobutylphenyl)propionic acid is a drug which has anti-inflammatory and analgesic properties. It is used for the treatment of rheumatoid arthritis or other inflammatory diseases of joints, soft tissue rheumatism and gout.

In general, a medicament suitable to combat acute pain is demanded to display its effects fast which is only achieved by a quick release and good bio-availability of the active ingredient.

Ibuprofen, although it is soluble in some physiologically compatible solvents, will immediately precipitate upon the addition of small amounts of water or when the solution is introduced into an aqueous medium as for example an artificial gastric juice. When such a solution, upon oral administration, gets into the stomach, the ibuprofen precipitates so that it will be barred from a quick resorption.

U.S. Pat. No. 4,690,823 describes soft gelatin capsules containing a solution of from 15 to 30 parts by weight of ibuprofen in from 70 to 85 parts by weight of polyoxyethylene-polyoxypropylene polymer or in a mixture of from 30 to 76 parts by weight of olyalkylene glycol and from 7 to 40 parts by weight of a surfactant. These capsules are described to have a very rapid and high bio-availability of the active ingredient. The active ingredient is not re-precipitated therefrom by aqueous media such as artificial gastric juice.

U.S. Pat. No. 4,690,823 furthermore discloses that ibuprofen may be readily dissolved in polyoxyethylene-polyoxypropylene polymer or in a mixture of a polyalkylene glycol and a surfactant at a temperature of from 45° C. to 65° C. and will remain in solution upon cooling to room temperature. No precipitation occurs when these solutions are introduced in an aqueous medium, more specifically into artificial gastric juice, so that the ibuprofen can be quickly and completely resorbed from this solution. Ibuprofen is used in an amount of up to 40% ibuprofen. No alkali hydroxide is added. In the examples polyoxyethylene-(40) [and-(60]-glycerol trihydroxystearate are used as surfactant.

U.S. Pat. No. 6,096,338 discloses a carrier system for a hydrophobic drug which comprises a) a digestible oil, b) a pharmaceutically acceptable surfactant, wherein the surfactant comprises a hydrophilic surfactant component which substantially inhibits the in vivo lipolysis of said digestible oil, and a lipophilic surfactant component capable of at least substantially reducing said inhibitory effesct of said hydrophilic surfactant component. Miglyol® 812 is disclosed as being often a preferred medium chain fatty acid triglyceride oil. Any pharmaceutically acceptable hydrophilic surfactants can be used. Among numerous examples Cremophor® EL and Cremophor® RH40 are mentioned as examples for the hydrophilic surfactant.

U.S. Pat. No. 5,141,961 relates to a process for solubilizing at least one difficultly soluble pharmaceutical active in a mixture of polyethylene glycol and polyvinylpyrrolidone.

WO 96/19202 discloses a solvent system for enhancing the solubility of ibuprofen which comprises as an ibuprofen solubility enhancer about 1% to 10% by weight of ammonium acetate. The solvent system is a pharmaceutically acceptable highly concentrated clear microcolloidal solution of ibuprofen suitable for filling soft gels for oral administration comprising, based on the weight of the clear solution, at least about 25% by weight of ibuprofen, about 1% to 10% by weight of water and about 50% to 74% by weight of at least one pharmaceutically acceptable solubilizing material selected from among non-ionic polyethoxylated surface active agents having a hydrophile lipophile balance within the range of 8 to 25, alone or in combination with a solvent system having a solubility parameter within the range of from 8.0 and 15.0.

WO 92/20334 discloses the use of S(−)sodium 2-(-isobutylphenylpropionate (the sodium salt of S(+)ibuprofen) in pharmaceutical compositions for the treatment of inflammation, pain and pyrexia. Liquid fill compositions suitably comprise a) 10–80% S(−)sodium 2-(4-isobutylphenyl)propionate and b) 20–90% of a fatty acid ester excipient which comprises one or more polyol esters and triglycerides of natural vegetable oil fatty acids.

WO 00/30619 discloses a self-emulsifying ibuprofen solution and soft gelatin capsule for use therewith. The solution provides a self-emulsifying ibuprofen formulation including a polyoxyethylene castor oil derivative and ibuprofen which increases the stability, concentration, and bioavailability of the scarcely water soluble ibuprofen. The amount of the polyoxyethylene castor oil derivatives ranges from approx. 30% to approx. 35% by weight.

In one preferred embodiment of the polyoxyethylene castor oil derivatives of WO 00/30619 the hydrophobic constituents comprise approx. 83% of the total mixture with the main component being glycerolpolyethylene glycol ricinoleate. The hydrophilic component (ca. 17%) consists of polyethylene glycols and glycerol ethoxylates.

In another preferred embodiment of the polyoxyethylene castor oil derivatives of WO 00/30619 the hydrophobic component is app. 75% of the total mixture. The hydrophobic component is comprised mainly of fatty acid esters of glycol polyethylene glycol and fatty esters of polyethylene glycol. The hydrophilic fraction (ca. 25%) consists of polyethylene glycols and glycerol ethoxylates.

The amount of ibuprofen in the formulation ranges from approx 33% to 38% by weight. In order to prevent the recrystallization of ibuprofen from the solution upon cooling, WO 00/30619 suggests to enhance and stabilize solution concentrations at ambient temperatures by the addition of complexing agents like soluble polyvinyl pyrrolidone (PVP).

The drug delivery vehicle of WO 00/30619 can be a two-piece, standard gelatin capsule, but is more preferably a soft gelatin capsule which is a one-piece, hermetically sealed gelatin capsule.

EP 0 413 171 B1 discloses agents for the treatment of conditions of severe pain consisting of soft gelatine capsules containing from 30 to 50 parts ibuprofen and from 1.5 to 4 parts bei weight of codein and/or physiologically compatible salts thereof, partially dissolved and partially suspended in 68.5 to 46 parts by weight of polyoxyethylene-polyoxypropylene-diol or in a mixture comprising 30 to 76 parts by weight of polyoxyethylene-polyoxypropylene-diol or polyethyleneglycol or polypropyleneglycol and from 7 to 40 parts by weight of a physiologically compatible surfactant.

U.S. Pat. No. 5,360,615 discloses a solvent system enhancing the solubility of pharmaceuticals for encapsulation, in particular, for enhancing the solubility of an acidic pharmaceutical agent like ibuprofen to produce a highly concentrated solution suitable for softgel filling comprising 10–80% polyethylene glycol, a solubility enhancing amount of either hydroxide or hydrogen ion and 1–20% by weight of water. Preferably, 0.2–1.0 mole equivalents of hydroxide ion per mole equivalent of acid in an acidic pharmaceutical agent is used.

The solution of ibuprofen disclosed in U.S. Pat. No. 5,360,615 as being suitable for filling softgels or two piece capsules, or for tablet formation comprises 40–80% by weight ibuprofen, 0.1–1.5 moles of hydroxide ion per mole of ibuprofen, 1–20% by weight water, and 4–12% by weight glycerin or propylene glycol in polyethylene glycol, wherein said hydroxide ion is more preferredly in the range of 0.2–0.5 moles of hydroxide ion per mole of ibuprofen.

It is one object of the present invention to provide a pharmaceutically acceptable clear solution for filling hard capsules which overcomes the above disadvantages of the prior art. The filled capsules should be usable as medicaments that can be readily taken and that may contain high concentrations of ibuprofen in a carrier, that are simple to prepare and that will quickly display a high activity. The solutions for filling hard shell capsules should show an increased stability and bioavailability of ibuprofen.

Hard shell capsules are two-piece pharmaceutical capsules with shells consisting generally known film forming materials or compositions. Suitable film forming material can be a hydrophilic polymer, gelatin being the preferred choice. Other suitable capsule shell materials include starch, modified starches like hydroxypropylated hydroxyethylated starches, casein, chitosan, soya bean protein, safflower protein, alginates, gellan gum, carrageenan, xanthan gum, pullulan, phtalated gelatin, succinated gelatin, cellulosephtalate-acetate, polyvinylalcohol, polyvinylacetate, hydroxypropyl methylcellulose, polyvinylacetate-phtalate, polymerisates of acrylic or mthacrylic esters or mixtures thereof. The capsule shell material may furthermore contain 0 to 40% pharmaceutically acceptable plasticizers based upon the weight of the hydrophilic polymer. The plasticizer which may be employed can be selected from polyethylene glycol, glycerol, sorbitol, dioctyl-sodium sulfosuccinate, triethyl citrate, tributyl citrate, 1,2-propyleneglycol, mono-, di, or tri-acetates of glycerol or mixtures thereof.

Additionally, the capsule shell material can contain 0 to 10% pharmaceutically acceptable lubricants based upon the weight of the hydrophilic polymer. The lubricate may be selected from aluminiumstearate, calciumstearate, magnesiumstearate, tinstearate, talc, sodium lauryl sulfate, lecithins, mineral oils, stearic acid or silicones or mixtures thereof.

Moreover, the capsule shell material can contain 0 to 10% pharmaceutically acceptable coloring agents based upon the weight of the hydrophilic polymer. The coloring agent may be selected from azo-quinophthalone-, triphenylmethane-, xanthene-dyes, iron oxides or hydroxides, titanium dioxide or natural dyes or mixtures thereof. Further suitable coloring agents are sunset yellow, allura red, amaranth, cochineal red, azogeranine, tartrazine, brilliant black, canthaxanthin, patent blue, fast green, brilliant blue, acid green, erythrosine, quinoline yellow, indigotine, curcumin or carbon black.

Furthermore, the capsule shell material contains 0 to 95% pharmaceutically acceptable extenders based upon the weight of the hydrophilic polymer. The extender may be selected from sunflower proteins, soybean proteins, cotton seed proteins, peanut proteins, rape seed proteins, lactose, gum arabic, acrylates or methacrylates, cellulose acetyl phthalates, hydroxypropyl cellulose, hydroxypropyl methylcellulose, hydroxypropyl methylcellulosephthalate, hydroxymethylcellulose, polyvinylpyrrolidone, shellac, bentonite, polyvinyl-acetatephtalate, phthalated gelatin, succinated gelatin, agar agar, hydroxyalkylstarches or mixtures thereof.

The solid pharmaceutical dosage form according to the present invention also may comprise a coating selected from cellacephate, polyvinyl acetate phthalate, methacrylic acid polymers, hypromellose phthalate, hydroxyalkyl methyl cellulose phthalates or mixtures thereof.

Preferably the film forming composition is suitable for the manufacture of clear transparent hard capsules by conventional dip molding process on high speed production equipment.

Accordingly, the present invention provides pharmaceutically acceptable solutions, which are preferably clear transparent, for filling hard shell capsules comprising, based upon the total weight of the solution,
a) from 35 to 75% by weight ibuprofen,
b) from 1 to 10% by weight alkali hydroxide, and
c) from 15 to 55% by weight of an emulsifier selected from polyoxyethylene alkyl ethers, medium chain triglycerides, propylene glycol esters, glyceryl esters, sorbitan esters, polyoxyethylene castor oil derivatives, polyoxyethylene sorbitan fatty acid esters, polyoxyethylene stearates, castor oil, or mixtures therof, wherein the molar ratio between alkali hydroxide b) and ibuprofen a) is from 0.1 to 0.5.

The present invention furthermore provides an ibuprofen-containing hard shell capsule, preferably clear transparent, containing a solution which comprises, based upon the total weight of the solution,
a) from 35 to 75% by weight ibuprofen,
b) from 1 to 10% by weight alkali hydroxide, and
c) from 15 to 55% by weight of an emulsifier selected from polyoxyethylene alkyl ethers, medium chain triglycerides, propylene glycol esters, glyceryl esters, sorbitan esters, polyoxyethylene castor oil derivatives, polyoxyethylene sorbitan fatty acid esters, polyoxyethylene stearates, castor oil, or mixtures therof, wherein the molar ratio between alkali hydroxide b) and ibuprofen a) is from 0.1 to 0.5.

As component a) ibuprofen is used according to the invention in an amount of from 35 to 75% by weight, preferably 40 to 55% by weight, most preferably 45 to 50 by weight, with respect to the total weight of the solution.

In the present invention ibuprofen is in general used as racemic mixture.

As component b) alkali hydroxide is used in an amount of from 1 to 10% by weight, preferably 1 to 5% by weight, with respect to the total weight of the solution.

The alkali hydroxide used as component b) in the present invention is preferably sodium hydroxide (NaOH), potassium hydroxide (KOH) or their mixture. The most preferred alkali hydroxide according to the invention is KOH.

In a preferred embodiment of the invention KOH is used in an amount of from 0.2 to 0.35 moles per mol ibuprofen, i.e., 0.2 to 0.35 mole equivalents of alkali hydroxide per mole of the pharmaceutical agent ibuprofen.

As component c) according to the invention 15 to 55% by weight, with respect to the total weight of the solution, emulsifiers selected from polyoxyethylene alkyl ethers, medium chain triglycerides, propylene glycol esters, glyceryl esters, sorbitan esters, polyoxyethylene castor oil derivatives, polyoxyethylene sorbitan fatty acid esters, polyoxyethylene stearates, or mixtures therof are used.

Preferred polyoxethylene alkyl ethers according to the invention are polyoxyl 2 cetyl ether, polyoxyl 10 cetyl ether, polyoxyl 20 cetyl ether, polyoxyl 4 lauryl ether, polyoxyl 23 lauryl ether, polyoxyl 2 oleyl ether, polyoxyl 10 oleyl ether, polyoxyl 20 oleyl ether, polyoxyl 2 stearyl ether, polyoxyl 10 stearyl ether, polyoxyl 20 stearyl ether, polyoxyl 100 stearyl ether or polyoxyl 20 cetostearyl ether.

Preferred medium chain triglycerides are caprylic/capric triglycerides like MTC oil, Miglyol® 810 or Miglyol® 812. Especially preferred is Miglyol® 812.

Preferred propylene glycol ester are propylene glycol propylene glycol dicocoate, propylene glycol distearate, propylene glycol dioctanoate, propylene glycol dipelargonate, propylene glycol diundecanoate, propylene glycol monostearate, propylene glycol monohydroxystearate, propylene glycol monolaurate, propylene glycol monomyristate, or propylene glycol monooleate. Especially preferred is propylene glycol monolaurate.

Preferred glyceryl esters are glyceryl monooleate, glyceryl monostearate or glyceryl palmitostearate. Especially preferred is glyceryl monooleate.

Preferred sorbitan ester are sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate or sorbitan tristearate. Especially preferred is sorbitan trioleate.

Preferred polyoxyethylene castor oil derivatives are polyoxyl 5 castor oil, polyoxyl 9 castor oil, polyoxyl 15 castor oil, polyoxyl 35 castor oil, polyoxyl 40 castor oil, polyoxyl 40 hydrogenated castor oil or polyoxyl 60 hydrogenated castor oil. Especially preferred are polyoxyl 35 castor oil (Cremophor® EL) or polyoxyl 40 hydrogenated castor oil (Cremophor® RH40).

Preferred polyoxyethylene sorbitan fatty acid esters are polysorbate 20, polysorbate 21, polysorbate 40, polysorbate 60, polysorbate 61, polysorbate 65, polysorbate 80, polysorbate 81, polysorbate 85 or polysorbate 120. Especially preferred is polysorbate 60.

Preferred polyoxyethylene stearates are polyoxyl 6 stearate, polyoxyl 8 stearate, polyoxyl 12 stearate or polyoxyl 20 stearate.

The density of the emulsifier c) may vary over a broad range, but is generally in the range of from 0.85 to 1.1 at 60° C.

Preferably, the emulsifier c) is a polyoxyethylene castor oil derivative, especially preferred polyoxyl 35 castor oil (Cremophor® EL) or polyoxyl 40 hydrogenated castor oil (Cremophor® RH40) in an amount of from 40 to 55, in particular 45 to 50% by weight of the whole composition.

In an especially preferred embodiment the polyoxyethylene castor oil derivative is used in an amount from 10 to 40%, more preferably from 15 to 35% by weight in admixture with medium chain triglycerides from 7 to 35% by weight, preferably 10 to 25% by weight, most preferably 12 to 18% by weight of the whole composition and whereby the caprylic/capric triglyceride Miglyol® 812 is especially preferred.

The solution according to the present invention comprising components a), b) and c) and/or water and/or other ingredients is preferably clear transparent and has in general a viscosity at 25° C. in the range of from 500 to 5000 cps, preferably of from 1000 to 4000 cps, and most preferably of from 1200 to 2500 cps.

In one aspect the present invention provides an ibuprofen-containing hard shell capsule containing the aforementioned solution comprising components a) to c) and/or water and/or other ingredients.

The hard shell capsule is a system comprised of the ibuprofen formulation and the capsule shell used to encapsulate the ibuprofen formulation. As such, not only is the filled ibuprofen formulation critical to produce the desired bioavailability characteristics but the shell composition is also critical as it must be compatible with the ibuprofen formulation. The potential fill-shell interactions could result in both physical and chemical capsule instability. Accordingly, the shell composition utilized to form the capsule for the ibuprofen dosage form is also critical to the present invention.

Therefore, the present invention utilizes a hard shell capsule consisting of the aforementioned film forming material.

Preferably, the capsule of the present invention is clear transparent.

Hard shell capsules for liquid filling have usually a volume of from 0.3 to 1.0 ml. The available volume is in general from 85–95 vol-%. In comparison to soft capsules, the moisture uptake of hard shell capsules is usually much lower than of soft capsules.

In the hard capsule encapsulation process the capsule is usually pre-fabricated and supplied empty, whereas in the soft capsule the encapsulation and filling take place simultaneously.

Various methods can be used to seal the hard shell capsules according to the invention. Preferred methods ar banding using a band consisting of a film forming material as aforementioned for the capsul shell, and sealing using a hydroalcoholic solution.

The banding of hard shell capsules is well-known in the art. The capsules are first rectified and then passed once or twice over a whell that revolves in a gelatin bath. An amount of gelatin is picked up by the serrated wheel and applied to the junction of the cap and body. The capsules remain in individual carries for drying.

According to the invention the hard shell capsule sealing is preferred which is based upon the lowering of the melting point of gelatin by the application of moisture to the area between the capsule body and cap.

In a preferred embodiment of the present invention a method is thus contemplated where the capsules are filled and then sealed by spraying a small amount of a water/ethanol mixture at the cap and body interface followed by warming to fuse the two capsule part together.

Instrumentation for performing the encapsulation according to the above methods is commercially available.

The capsules of the present invention did not show any capsule brittleness as determined according to Cadé and Madit, in "Liquid Filling in Hard Gelatin Capsules—Preliminary Steps", Bulletin Technique Gattefosse, 1996, when stored at 30% and 50% relative humidity for four weeks.

Using the solution of the present invention, it is possible to prepare a unit dose of ibuprofen in a two piece hard shell capsule, wherein the fill solution contains a therapeutically effective amount of ibuprofen dissolved within. The dosages administered will vary depending upon the acidic pharmaceutical agent employed, the mode of administration the treatment desired, the size, age, and weight of the patient being treated and the like.

The invention will be further illustrated by the following non-limiting examples. Percentages given therein refer to the total weight of the solution.

EXAMPLES

Example 1

EXAMPLE 1

|  | mg/caps | % |
|---|---|---|
| Ibuprofen | 200.00 | 47.62 |
| Cremophor ® RH40 | 140.71 | 33.50 |
| Miglyol ® 812 | 63.00 | 15.00 |
| KOH | 16.29 | 3.88 |
|  | 420.00 | 100 |

In Example 1 0.3 mol equiv KOH and 15% Miglyol® were used. The viscosity at 25° C. was 1900 cps and at 35° C. 836 cps.

EXAMPLE 2

|  | mg/caps | % |
|---|---|---|
| Ibuprofen | 200.00 | 47.62 |
| Cremophor ® EL | 140.71 | 33.50 |
| Miglyol ® 812 | 63.00 | 15.00 |
| KOH | 16.29 | 3.88 |
|  | 420.00 | 100 |

In Example 2 0.3 mol equiv KOH/15% Miglyol® were used. The viscosity was 3140 cp at 25° C.

Similarly to Examples 1 and 2 examples were produced which corresponded to the following compositions.

|  | mg/caps | % |
|---|---|---|
| Example 3 |  |  |
| Ibuprofen | 201.78 | 48.04 |
| Cremophor ® EL or RH 40 | 201.78 | 48.04 |
| Miglyol ® 812 | — | — |
| KOH | 16.44 | 3.92 |
|  | 420.00 | 100 |
| Examples 4 and 5 |  |  |
| Ibuprofen | 201.43 | 38.74 |
| Cremophor ® EL (Example 4) or RH40 (Ex. 5) | 151.07 | 29.05 |
| Miglyol ® 812 | 151.07 | 29.05 |
| KOH | 16.42 | 3.16 |
|  | 520.00 | 100 |

The invention claimed is:

1. A pharmaceutically acceptable composition in the form of a solution for a liquid filling for a hard shell capsule comprising, based upon the total weight of the composition,
   a) from 35 to 75% by weight of a racemic mixture of ibuprofen,
   b) from 0.2 to 0.35 mole equivalents of an alkali hydroxide selected from the group consisting of sodium hydroxide and potassium hydroxide per mole of ibuprofen,
   c) from 40 to 55% by weight of an emulsifier which is a polyoxyethylene castor oil derivative and d) from 12 to 18% weight of a medium chain triglyceride, having a density in the range of 0.85–1.1 at 60 degrees C. and selected from the group consisting of
   (i) a polyoxoethylene alkyl ether selected from the group consisting of polyoxyl 2 cetyl ether, polyoxyl 10 cetyl ether, polyoxyl 20 cetyl ether, polyoxyl 4 lauryl ether, polyoxyl 23 lauryl ether, polyoxyl 2 oleyl ether, polyoxyl 10 oleyl ether, polyoxyl 20 oleyl ether, polyoxyl 2 stearyl ether, polyoxyl 10 stearyl ether, polyoxyl 2 stearyl ether, polyoxyul 10 stearyl ether, polyoxyl 20 stearyl ether, polyoxyl 100 stearyl ether polyoxyl 20 cetostearyl ether and mixtures thereof;
   (ii) a propylene glycol ester selected from the group consisting of propylene glycol dicocoate, propylene glycol distearate, propylene glycol dioctanoate, propylene glycol dipelargonate, propylene glycol diundecanoate, propylene glycol monostearate, propylene glycol monohydroxystearate, propylene glycol monolaurate, propylene glycol monomyristate, propylene glycol monooleate and mixtures thereof;
   (iii) a glyceryl ester selected from the group consisting of glyceryl monooleate, glyceryl monostearate, glyceryl palmitosterate and mixtures thereof;
   (iv) a sorbitan ester selected from the group consisting of sorbitan di-isostearate, sorbitan dioleate, sorbitan monolaurate, sorbitan monoisosterate, sorbitan monooleate, sorbitan monopalmitate, sorbitan monostearate, sorbitan sesqui isostearate, sorbitan tri-isostearate, sorbitan trioleate, sorbitan tristearate and mixtures thereof;
   (v) a polyoxyethylene castor oil derivative selected from the group consisting of polyoxy 5 castor oil, polyoxy 9 castor oil, polyoxy 15 castor oil, polyoxyl 35 castor oil, polyoxyl 40 castor oil, polyoxyl 40 hydrogenated castor oil, polyoxyl 60 hydrogenated castor oil and mixtures thereof;
   (vi) a polyoxyethylene sorbitan fatty ester selected from the group consisting of polysorbate 20, polysorbate 21, polysorbate 40, polysorbate 60, polysorbate 61, polysorbate 65, polysorbate 80, polysorbate 81, polysorbate 85, polysorbate 120 and mixtures thereof;
   (vii) a polyoxyethylene stearate selected from the group consisting of polyoxyl 6 stearate, polyoxyl 8 stearate, polyoxyl 12 stearate, polyoxyl 20 stearate and mixtures thereof; and mixtures of (i)–(vii),] and wherein the viscosity of the composition is in the range of 1000–4000 cps at 25 degrees C.

2. A pharmaceutical composition according to claim 1, wherein the emulsifier c) is polyoxyl 35 castor oil or polyoxyl 40 hydrogenated castor oil.

3. A pharmaceutical composition according to claim 2, wherein the emulsifier c) is contained in an amount from 45 to 50% by weight.

4. A pharmaceutical composition according to claim 1, wherein the emulsifier c) is a mixture of polyoxyl 35 castor oil or polyoxyl 40 hydrogenated castor oil and which composition additionally comprises caprylic/capric triglyceride.

5. A liquid filled pharmaceutical hard capsule containing a composition in the form of a solution which comprises, based upon the total weight of the composition,
   a) from 35 to 75% by weight of a racemic mixture of ibuprofen,
   b) from 0.2 to 0.35 mole equivalents of an alkali hydroxide selected from the group consisting of sodium hydroxide and potassium hydroxide per mole of ibuprofen, c) from 40 to 55% by weight of an emulsifier which is a polyoxyethylene castor oil derivative and d) from 12 to 18% by weight of a medium chain triglyceride, having a density in the range of 0.85–1.1 at 60 degrees C. and selected from the group consisting of
(i) a polyoxoethylene alkyl ether selected from the group consisting of polyoxyl 2 cetyl ether, polyoxyl 10 cetyl ether, polyoxyl 20 cetyl ether, polyoxyl 4 lauryl ether, polyoxyl 23 lauryl ether, polyoxyl 2 oleyl ether, polyoxyl 10 oleyl ether, polyoxyl 20 oleyl ether, polyoxyl 2 stearyl ether, polyoxyl 10 stearyl ether, polyoxyl 2 stearyl ether, polyoxyul 10 stearyl ether, polyoxyl 20 stearyl ether, polyoxyl 100 stearyl ether polyoxyl 20 cetostearyl ether and mixtures thereof
(ii) a propylene glycol ester selected from the group consisting of propylene glycol dicocoate, propylene glycol distearate, propylene glycol dioctanoate, propylene glycol dipelargonate, propylene glycol diundecanoate, propylene glycol monostearate, propylene glycol monohydroxystearate, propylene glycol monolaurate, propylene glycol monomyristate, propylene glycol monooleate and mixtures thereof;
(iii) a glyceryl ester selected from the group consisting of glyceryl monooleate, glyceryl monostearate, glyceryl palmitosterate and mixtures thereof;
(iv) a sorbitan ester selected from the group consisting of sorbitan di-isostearate, sorbitan dioleate, sorbitan monolaurate, sorbitan monoisosterate, sorbitan monooleate, sorbitan monopalmitate, sorbitan monostearate, sorbitan sesquiisostearate, sorbitan tri-isostearate, sorbitan trioleate, sorbitan tristearate and mixtures thereof
(v) a polyoxyethylene castor oil derivative selected from the group consisting of polyoxy 5 castor oil, polyoxy 9 castor oil, polyoxy 15 castor oil, polyoxyl 35 castor oil, polyoxyl 40 castor oil, polyoxyl 40 hydrogenated castor oil, polyoxyl 60 hydrogenated castor oil and mixtures thereof;
(vi) a polyoxyethylene sorbitan fatty ester selected from the group consisting of polysorbate 20, polysorbate 21, polysorbate 40, polysorbate 60, polysorbate 61, polysorbate 65, polysorbate 80, polysorbate 81, polysorbate 85, polysorbate 120 and mixtures thereof;
(vii) a polyoxyethylene stearate selected from the group consisting of polyoxyl 6 stearate, polyoxyl 8 stearate, polyoxyl 12 stearate, polyoxyl 20 stearate and mixtures thereof;

and mixtures of (i)–(vii),] and wherein the viscosity of the composition is in the range of 1000–4000 cps at 25 degrees C.

6. A liquid filled pharmaceutical hard capsule containing a composition according to claim 3.

7. A liquid filled pharmaceutical hard capsule containing a composition according to claim 1.

8. A composition according to any one of claims 2, 3 and 4 wherein the viscosity of the composition is in the range of 1200–2500 cps at 25 degrees C.

9. A liquid filled pharmaceutical hard capsule according to any one of claims 5–7 wherein the capsule is clear and transparent and the composition contained therein is in the form of a solution of ibuprofen.

\* \* \* \* \*